(12) United States Patent
Zou et al.

(10) Patent No.: US 12,201,754 B2
(45) Date of Patent: Jan. 21, 2025

(54) DEVICE FOR ATOMIZATION OF WATER AND ESSENTIAL OIL

(71) Applicant: Shenzhen Jingxintai Houseware Co., Ltd., Shenzhen (CN)

(72) Inventors: Jinshan Zou, Shenzhen (CN); Bo Fan, Shenzhen (CN)

(73) Assignee: SHENZHEN JINGXINTAI HOUSEWARE CO., LTD., Shenzhen (CN)

(*) Notice: Subject to any disclaimer, the term of this patent is extended or adjusted under 35 U.S.C. 154(b) by 0 days.

(21) Appl. No.: 17/528,137

(22) Filed: Nov. 16, 2021

(65) Prior Publication Data
US 2022/0072183 A1 Mar. 10, 2022

Related U.S. Application Data

(63) Continuation-in-part of application No. PCT/CN2019/090569, filed on Jun. 10, 2019.

(30) Foreign Application Priority Data

May 29, 2019 (CN) .......................... 201910457155.0

(51) Int. Cl.
A61L 9/14 (2006.01)
A61M 11/02 (2006.01)
B05B 7/02 (2006.01)
B05B 7/04 (2006.01)
B05B 7/24 (2006.01)

(52) U.S. Cl.
CPC ................ *A61L 9/14* (2013.01); *A61M 11/02* (2013.01); *B05B 7/025* (2013.01); *B05B 7/0408* (2013.01); *B05B 7/2491* (2013.01)

(58) Field of Classification Search
CPC .......... A61L 9/14; A61M 11/02; B05B 7/025; B05B 7/0408; B05B 7/2491
USPC ........................... 239/102.1, 102.2, 340, 351
See application file for complete search history.

(56) References Cited

U.S. PATENT DOCUMENTS 7,963,460 B2 * 6/2011 Jorgensen ............... A61L 9/122
239/289
7,992,801 B2 * 8/2011 Jorgensen ................ A61L 9/14
239/289

(Continued)

*Primary Examiner* — Christopher S Kim
(74) *Attorney, Agent, or Firm* — MATTHIAS SCHOLL P.C.; Matthias Scholl

(57) ABSTRACT

A device for atomization of water and essential oil includes a water atomization assembly, an essential oil atomization assembly, and a vacuum pump. The water atomization assembly includes a first housing, a water container disposed in the first housing, an ultrasonic atomization module disposed in the first housing to atomize water from the water container. The essential oil atomization assembly includes a second housing, an essential oil atomization module disposed in the second housing, and an essential oil container. The vacuum pump is fixedly disposed on a bottom end of the first housing. The essential oil atomization module is connected to and disposed above the essential oil container; the essential oil container is at least partially disposed in the second housing; the first housing includes an outer wall including a recess, and the second housing is fixedly embedded in an upper part of the recess.

12 Claims, 6 Drawing Sheets

(56) References Cited

U.S. PATENT DOCUMENTS

| | | | |
|---|---|---|---|
| 2010/0084484 A1* | 4/2010 | Sevy | A61M 11/001 |
| | | | 239/340 |
| 2014/0263722 A1* | 9/2014 | Hsiao | A61L 9/122 |
| | | | 239/102.2 |
| 2019/0249888 A1* | 8/2019 | Chiu | A61L 9/14 |
| 2020/0147257 A1* | 5/2020 | Chiu | A61L 9/14 |
| 2022/0111411 A1* | 4/2022 | Panton | H01M 10/0525 |
| 2023/0084119 A1* | 3/2023 | Zhang | A24F 40/485 |
| | | | 239/102.2 |

* cited by examiner

DEVICE FOR ATOMIZATION OF WATER AND ESSENTIAL OIL

CROSS-REFERENCE TO RELATED APPLICATIONS

This application is a continuation-in-part of International Patent Application No. PCT/CN2019/090569 with an international filing date of Jun. 10, 2019, designating the United States, now pending, and further claims foreign priority benefits to Chinese Patent Application No. 201910457155.0 filed May 29, 2019. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, MA 02142.

BACKGROUND

The disclosure relates to a device for atomization of water and essential oil.

Conventionally, essential oil diffusers and humidifiers are two kinds of independent products. That is, conventional essential oil diffusers do not have humidification function, and the humidifiers do not have aroma-diffusing function. In addition, conventional essential oil diffusers take the vacuum pump as a core unit, and the atomization unit is directly fixedly or movably connected to the vacuum pump, with the vacuum pump or a nozzle directly connected to the vacuum pump as a fixed base point. The design poses high requirements on the air tightness and the structural strength of the essential oil diffusers so as to bear the external force in the direction different from the direction of the connection of the components, for example, external pulling force when installing or removing the essential oil container, as well as the gravity of the essential oil container, etc. Thus, the related technical solutions that the atomization unit is directly fixedly or movably connected to the vacuum pump make the essential oil diffusers complex, costly, and non-durable.

SUMMARY

The disclosure provides a device for atomization of water and essential oil comprising a water atomization assembly, an essential oil atomization assembly, and a vacuum pump. The water atomization assembly comprises a first housing, a water container disposed in the first housing, an ultrasonic atomization module disposed in the first housing to atomize water from the water container. The essential oil atomization assembly comprises a second housing, an essential oil atomization module disposed in the second housing, and an essential oil container. The vacuum pump is fixedly disposed on a bottom end of the first housing. The essential oil atomization module is connected to and disposed above the essential oil container; the essential oil container is at least partially disposed in the second housing; the first housing comprises an outer wall comprising a recess, and the second housing is fixedly embedded in an upper part of the recess; the vacuum pump comprises a flexible tube connected to the essential oil atomization module to provide compressed air to atomize an essential oil from the essential oil container.

In a class of this embodiment, the second housing comprises an inner side wall and a mounting member protruding from the inner side wall; and the essential oil atomization module is fixed on the mounting member through a screw fastener.

In a class of this embodiment, the mounting member comprises two mounting columns protruding from the second housing; and the essential oil atomization module comprises screw holes corresponding to the two mounting columns in positions and sizes.

In a class of this embodiment, the essential oil atomization module comprises a nozzle, an upper cover, a partition, and a lower cover; the nozzle is disposed on a side wall of the lower cover; the partition is disposed on the lower cover; the partition and the lower cover form an atomization chamber, and the partition and the upper cover form an accommodation chamber; the partition comprises an air channel, and the atomization chamber communicates with the accommodation chamber via the air channel.

In a class of this embodiment, the lower cover comprises a first through hole and a second through hole, both communicating with the atomization chamber; the first through hole is disposed on a lower part of the lower cover; the second housing further comprises a bottom opening; the essential oil container comprises a head passing through the bottom opening of the second housing to communicate with the first through hole; the second through hole is disposed on a side part of the lower cover to receive the nozzle; one end of the nozzle close to the atomization chamber is connected to an air duct, and the compressed air passes through the nozzle and the air duct and enters the atomization chamber; another end of the air duct is provided with and communicates with a straw; the straw extends through the head and into the essential oil container.

In a class of this embodiment, the atomization chamber comprises a first inner wall and a first outer wall; the accommodation chamber comprises a second inner wall and a second outer wall; the first inner wall comprises a step and the partition is supported by the step; the first outer wall comprises a groove and the second outer wall is imbedded in the groove; the second outer wall comprises a protrusion corresponding to the groove in position and shape, and the upper cover is integrated with the lower cover via the cooperation of the protrusion and the groove.

In a class of this embodiment, the partition comprises a main body and a spiral duct disposed in a central part of the main body; the spiral duct comprises a first opening disposed on a top surface of the main body and a second opening disposed on a bottom surface of the main body; and the essential oil atomized in the atomization chamber enters the accommodation chamber through the spiral duct.

In a class of this embodiment, a height of the step is equal to that of an edge of the main body; the partition is disposed on the step, and the edge of the main body abuts against and is flush with the first inner wall of the atomization chamber; the upper cover is connected to the lower cover, and the second inner wall of the accommodation chamber abuts against the edge of the main body and the first inner wall of the atomization chamber to fix the partition.

In a class of this embodiment, the water container comprises a bottom wall provided with a water outlet; the water atomization assembly further comprises a water passage communicating with the water outlet, a vapor passage, and a blower; the ultrasonic atomization module is disposed below the water passage; the blower is fixedly disposed on the bottom end of the first housing and is configured to produce airflow to drive vapor in the vapor passage to flow out.

In a class of this embodiment, a buoy valve is disposed between the water outlet and the water passage; the buoy valve comprises a control valve disposed at the water outlet and a telltale float disposed in the water passage and matched with the control valve.

In a class of this embodiment, the device further comprises a third housing and a control unit disposed in the third housing; the control unit is configured to control a working time and/or working state of the ultrasonic atomization module and the essential oil atomization module; and the third housing is fixedly embedded in a lower part of the recess.

The following advantages are associated with the device for atomization of water and essential oil of the disclosure:

The device of the disclosure comprises the water atomization assembly and the essential oil atomization assembly. The water container is disposed in the first housing, and the essential oil atomization module is disposed in the second housing. The vacuum pump comprises the flexible tube connected to the essential oil atomization module. In this way, the device has the dual function of atomization of water and essential oil. In addition, the essential oil atomization assembly is not in direct connection with the vacuum pump and is fixed in the second housing. Thus, the connection of the vacuum pump and the essential oil atomization assembly is easy to realize, and the requirements of the structural strength of the components of the essential oil atomization assembly is slightly reduced compared with conventional essential oil diffusers, thus saving the structural and manufacturing costs.

DETAILED DESCRIPTION

To further illustrate, embodiments detailing a device for atomization of water and essential oil are described below. It should be noted that the following embodiments are intended to describe and not to limit the disclosure.

Figure 1:
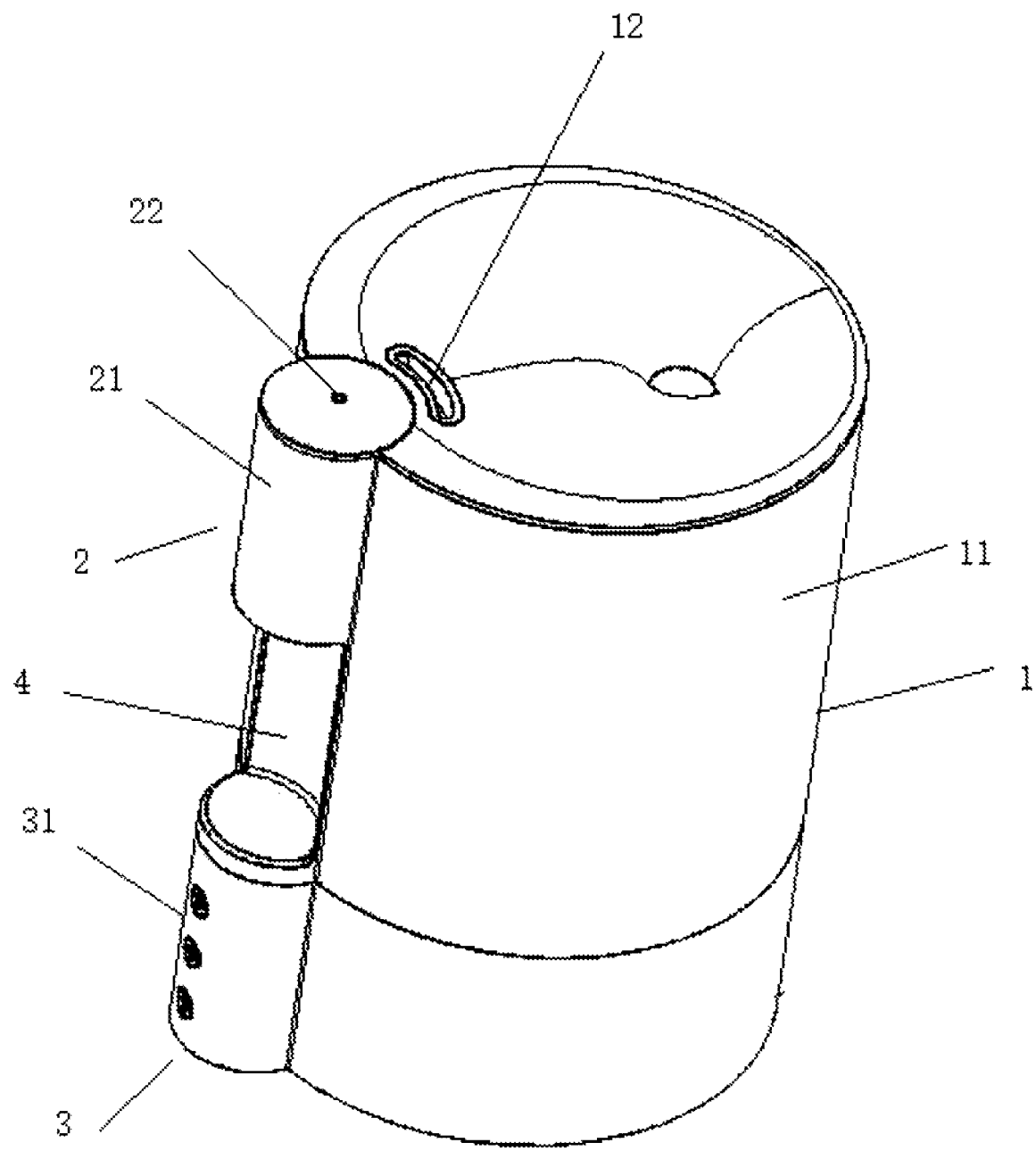
FIG. 1 is a schematic diagram of a device for atomization of water and essential oil according to one embodiment of the disclosure.
Figure 2:
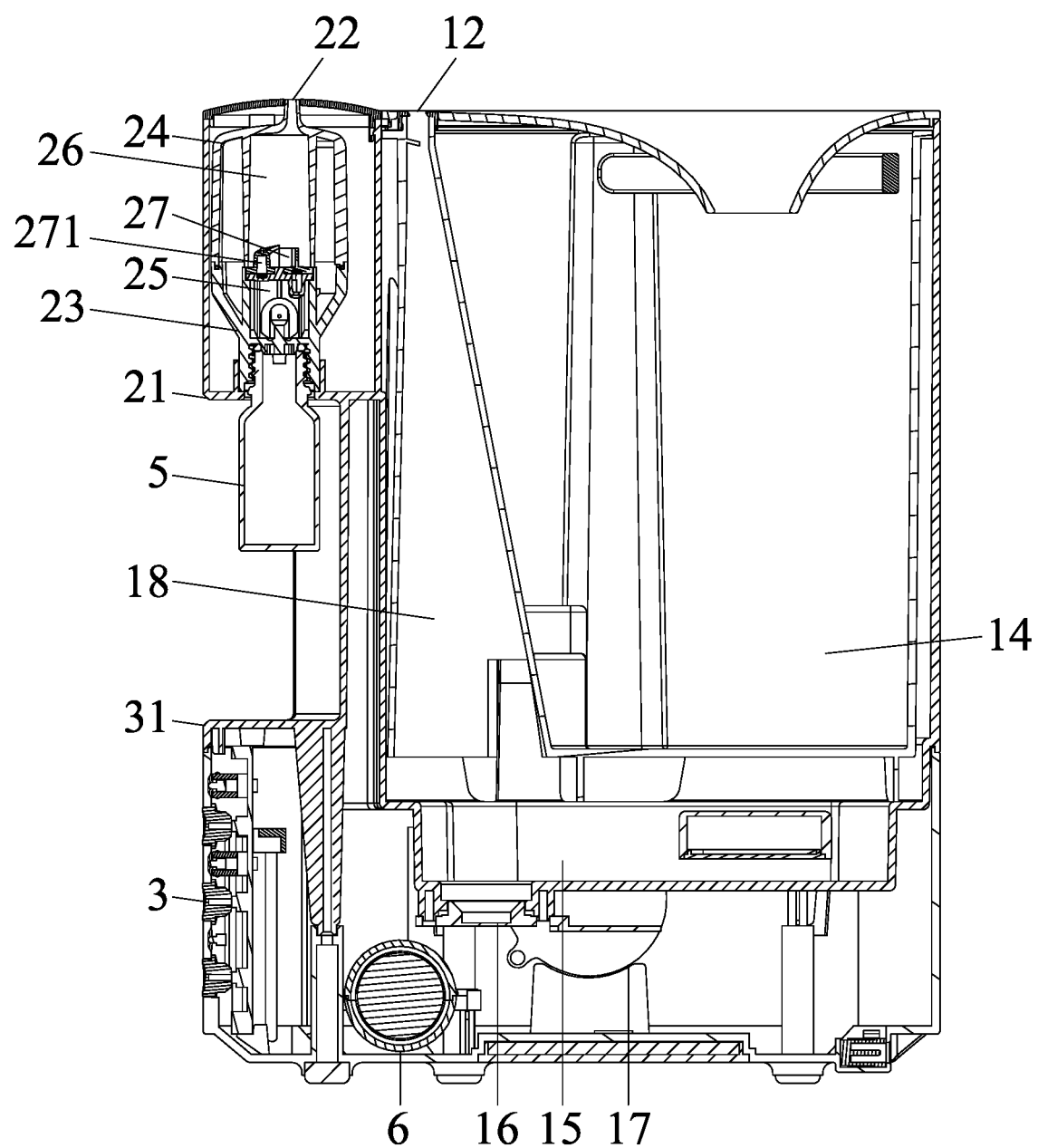
FIG. 2 is a sectional view of a device for atomization of water and essential oil according to one embodiment of the disclosure.
Figure 3:
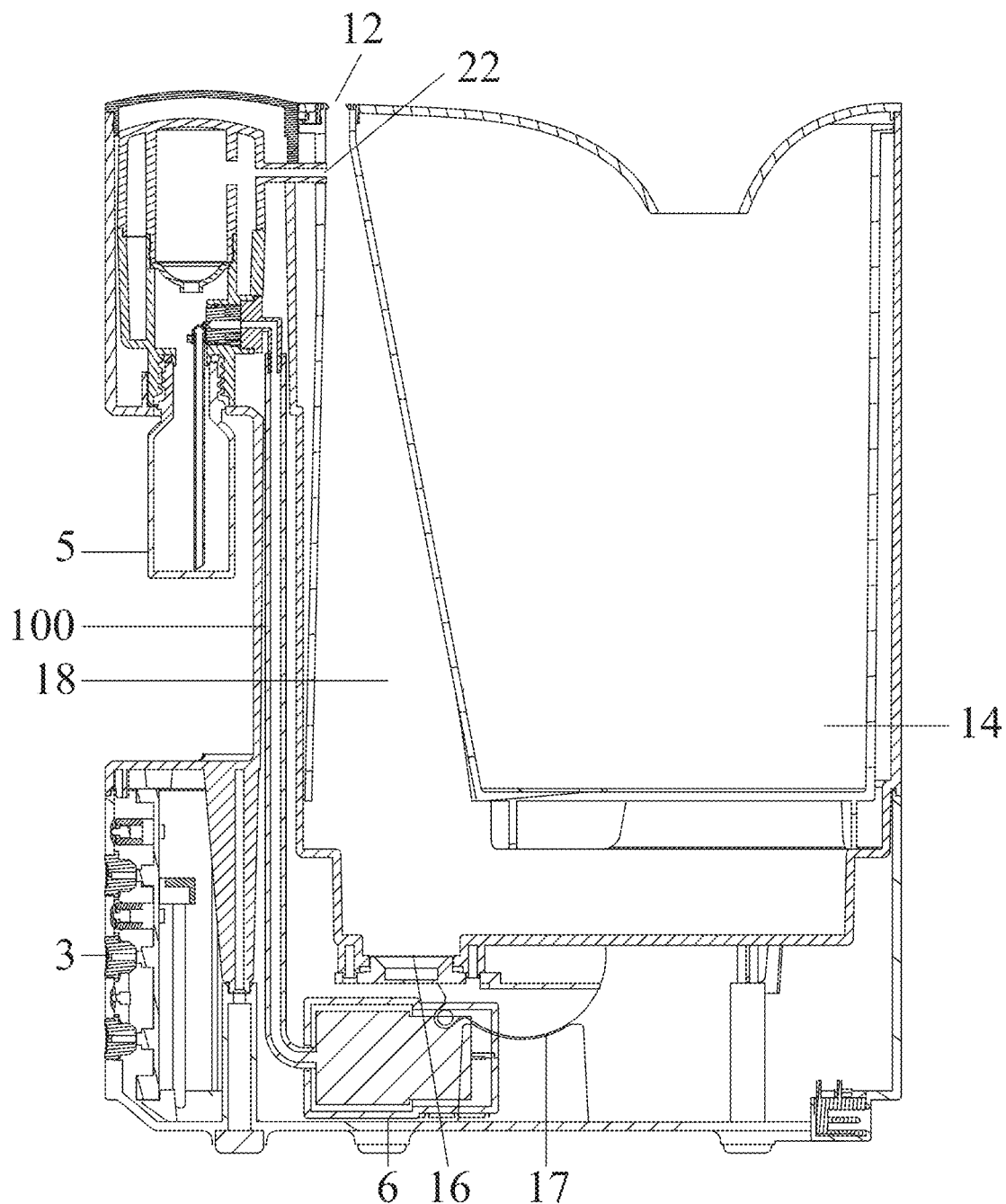
FIG. 3 is a sectional view of a device for atomization of water and essential oil according to another embodiment of the disclosure.

As shown in FIGS. 1-2, a device for atomization of water and essential oil of the disclosure comprises a water atomization assembly 1, an essential oil atomization assembly, and a vacuum pump 6. The water atomization assembly 1 comprises a first housing 11, a water container 14 disposed in the first housing 11, an ultrasonic atomization module 16 disposed in the first housing 11. The ultrasonic atomization module 16 is configured to atomize water from the water container into water mist and leave out of the water atomization assembly.

The essential oil atomization assembly comprises a second housing 21, an essential oil atomization module 2 disposed in the second housing, and an essential oil container 5. The essential oil atomization module 2 is connected to and disposed above the essential oil container 5; the essential oil container is at least partially disposed in the second housing 21.

The vacuum pump 6 comprises a flexible tube 100 connected to the essential oil atomization module to provide compressed air to atomize an essential oil from the essential oil container. That is to say, the vacuum pump 6 provides an airflow to the essential oil atomization module 2, and the essential oil atomization module 2 is configured to pump the essential oil from the essential oil container 5 in the presence of the airflow and atomize the essential oil, and the atomized essential oil flows out of the essential oil container under the drive of the airflow.

The first housing 11 comprises an outer wall comprising a recess 4, and the second housing 21 is fixedly embedded in the upper part of the recess 4. The vacuum pump 6 is fixedly disposed on the bottom end of the first housing 11.

Figure 6:
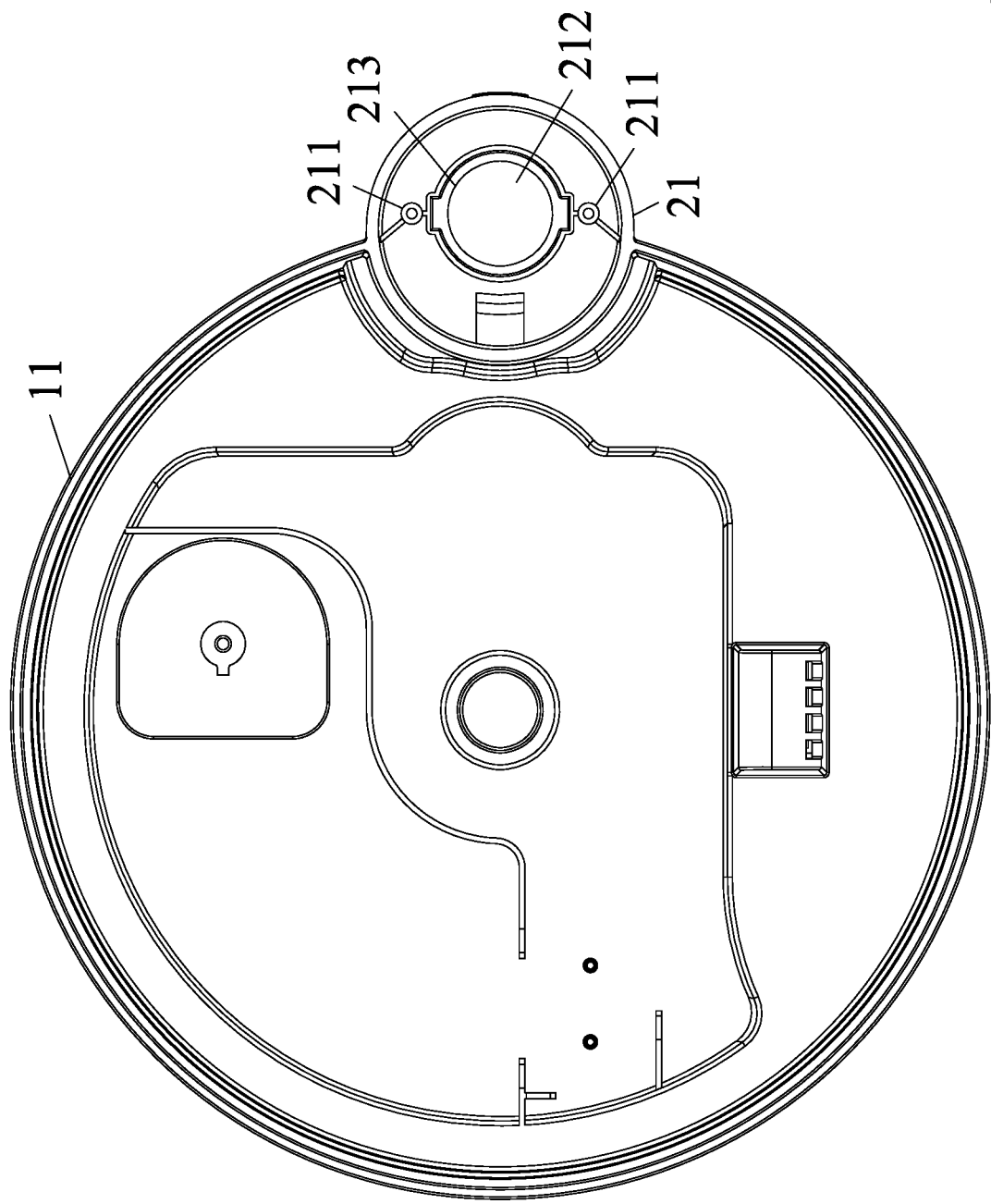
FIG. 6 is a schematic diagram of a mounting member according to one embodiment of the disclosure.

The second housing 21 comprises an inner side wall and a mounting member protruding from the inner side wall; and the essential oil atomization module 2 is fixed on the mounting member through a screw fastener. In this way, the essential oil atomization module 2 is not directly fixed on the vacuum pump 6, and the stress direction of each component is consistent with the gravity direction of the essential oil container 5, thus reducing the airtight requirement between the components, saving the cost and improving the durability. Specifically, in FIG. 6, the mounting member comprises two mounting columns 211 protruding from the second housing 21; and the essential oil atomization module 2 comprises screw holes (not shown in the drawings) corresponding to the two mounting columns 211 in positions and sizes. During installation, the essential oil atomization module 2 is disposed in the second housing 21, and the mounting screws are embedded in the screw holes of the two mounting columns 211, so that the integral essential oil atomization module 2 is fixed in the second housing 21. To further stabilize the essential oil atomizing module 2 in the second housing, in certain embodiments, the second housing 21 further comprises a bottom opening 212. The essential oil container comprises a head detachably disposed in the bottom opening. Thus, the essential oil container 5 can be quickly installed or removed from the second housing 21 after installation. Furthermore, the second housing further comprises a flange 213 encircling the bottom opening 212. When the essential oil atomization module 2 is disposed in the second housing 21 through the mounting screws, the bottom end of the essential oil atomization module 2 abuts against the flange 213, so that the essential oil atomization module 2 is firmly fixed in the second housing 21.

Figure 4:
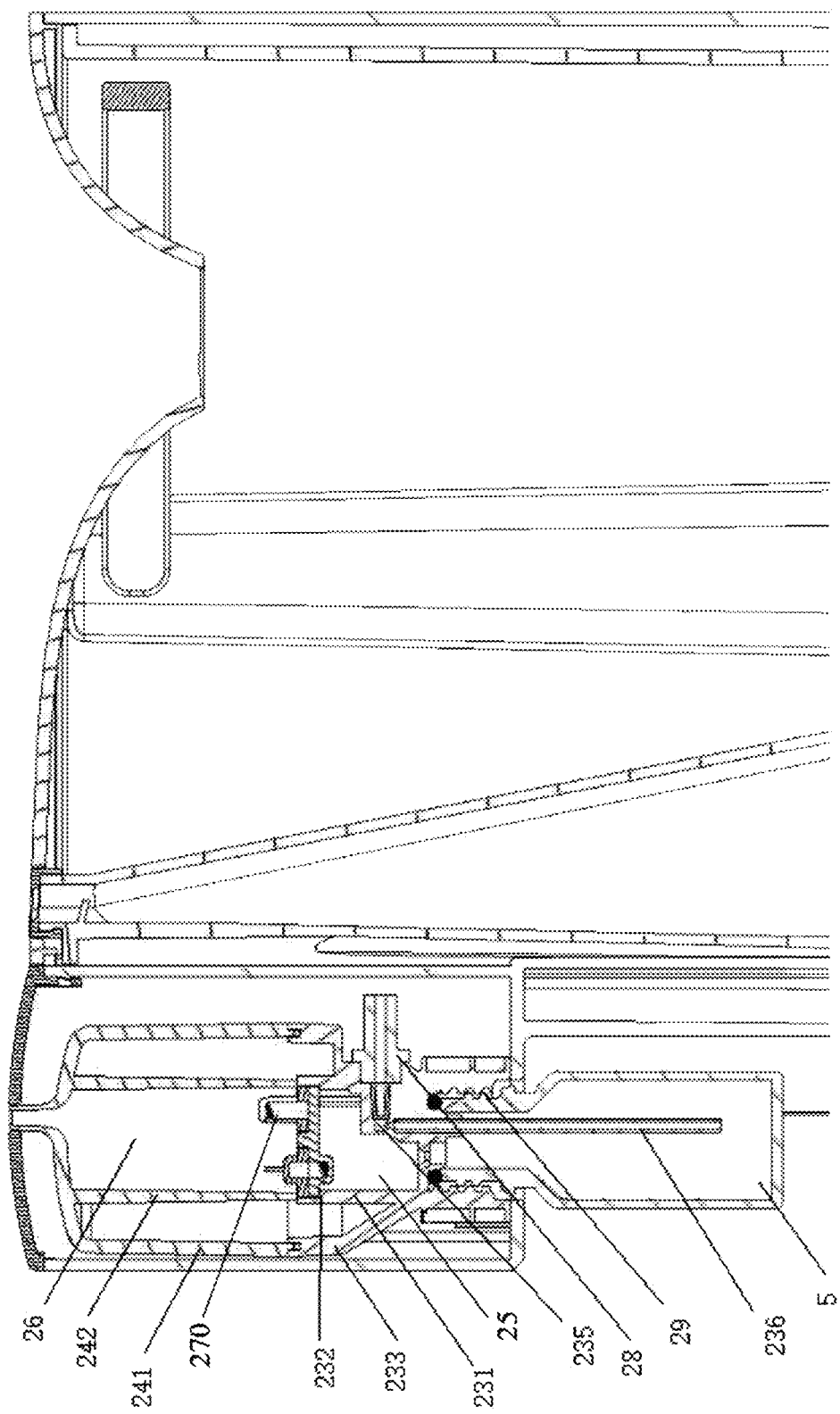
FIG. 4 is a sectional view of a second housing of a device for atomization of water and essential oil according to one embodiment of the disclosure.
Figure 5:
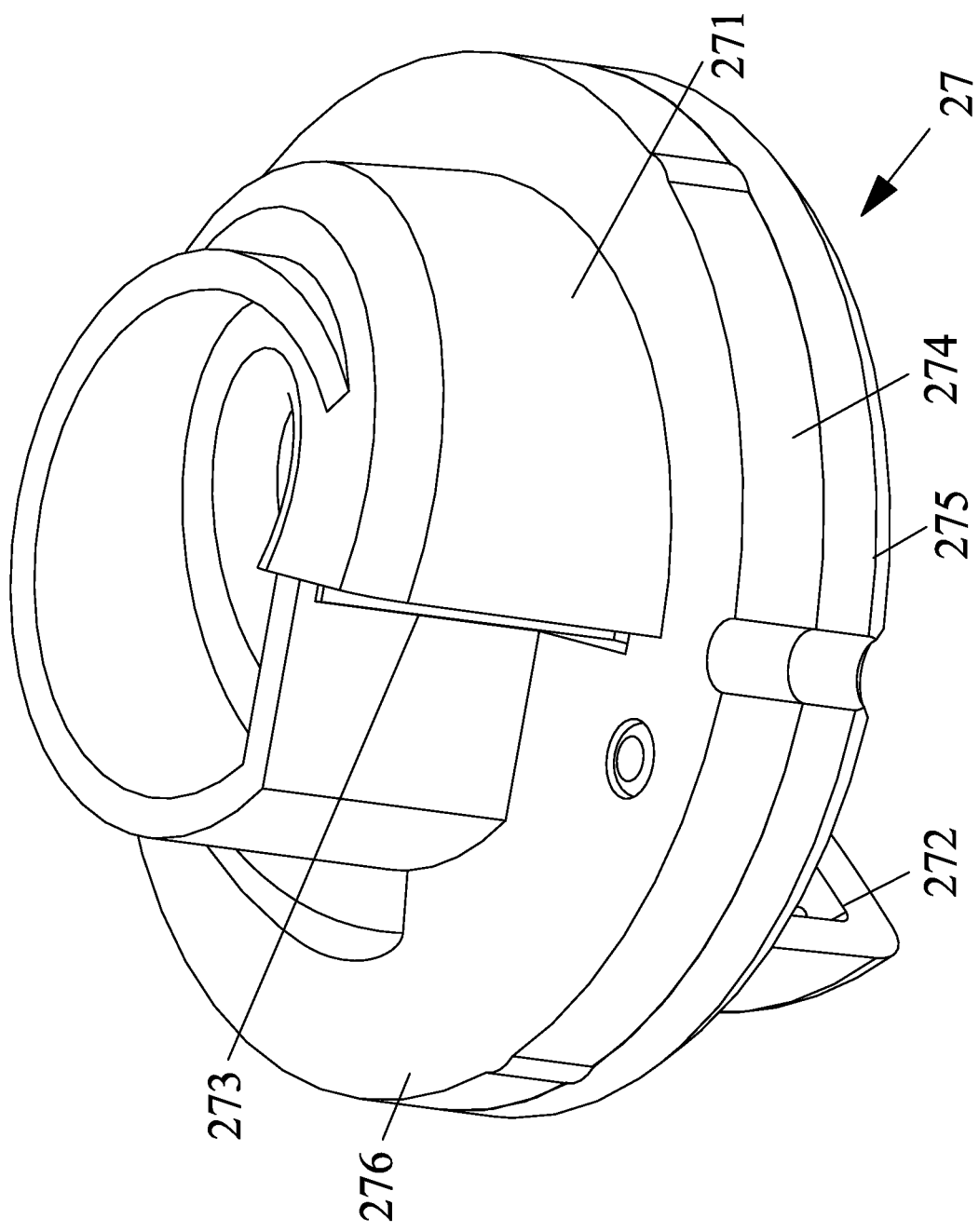
FIG. 5 is a schematic diagram of a partition according to one embodiment of the disclosure.

As shown in FIGS. 2 and 4, the essential oil atomization module 2 comprises a nozzle 28, an upper cover 24, a partition 27, and a lower cover 23. The screw holes are disposed on the lower cover 23 or the upper cover 24. The lower cover 23 and the upper cover 24 are connected to each other to form a cavity, and the partition 27 is disposed in the lower cover 23, and the upper cover 24 covers the lower cover 23 on which the partition 27 is placed. The partition 27 and the lower cover 23 form an atomization chamber 25, and the partition 27 and the upper cover form an accommodation chamber 26; the partition 27 comprises an air channel 271, and the atomization chamber communicates with the accommodation chamber via the air channel. Although the air channel of the disclosure employs a spiral duct, optionally, one or more through holes can be disposed on the partition as the air channel, which reduces the processing costs without affecting the atomization of the essential oil.

The lower cover 23 comprises a first through hole 29 and a second through hole, both communicating with the atomization chamber; the first through hole 29 is disposed on the lower part of the lower cover 23; the essential oil container 5 comprises a head passing through the bottom opening of the second housing 21 to communicate with the first through hole 29; the second through hole is disposed on the side part of the lower cover 23 to receive the nozzle 28; one end of the nozzle close to the atomization chamber is connected to an air duct 235, and the air flow passes through the nozzle 28 and the air duct 235 and enters the atomization chamber 25; another end of the air duct 235 is provided with and communicates with a straw 236; the straw 236 extends through the head and into the essential oil container 5.

In this example, the vacuum pump 6 operates to produce compressed air and air flow. The compressed air and air flow are conveyed to the nozzle 28 via the flexible tube 100. When the air flow passes through the nozzle 28, owing to the narrow size of the air passage of the nozzle 28, the air pressure of the air flow increases, and the high-pressure air flow enters the atomization chamber 25 through the air duct 235. Therefore, a negative pressure is formed in the air duct 235, so that the liquid essential oil in the essential oil container 5 enters the air duct 235 through the straw 236 and is impacted into droplets by the high-pressure air flow. The droplets enter the atomization chamber 25 and rams into the side wall of the atomization chamber 25 to further decompose into smaller droplets thus realizing the atomization of the essential oil. The atomized essential oil is pushed to a higher position by the subsequent air flow and enters the accommodation chamber 26 through the air duct 271 on the partition 27. When the atomized essential oil in the accommodation chamber 26 accumulates to a certain amount, part of the atomized essential oil entering in the early stage overflows through the perfume outlet 22 on the top of the second housing 21 under the drive of the atomized essential oil entering in the later stage, and is dispersed in the ambient air to produce fragrant smell.

In this example, the upper cover 24, the lower cover 23, and the partition 27 form an entire structure, together with the nozzle 28 and the essential oil container 5 disposed on the lower cover 23, the essential oil atomization assembly is assembled. Specifically, the partition 27 is disposed on the lower cover 23, and the upper cover 24 covers the partition and the lower cover. Structurally, the atomization chamber comprises a first inner wall 231 and a first outer wall 233; the accommodation chamber comprises a second inner wall 242 and a second outer wall 241. The first inner wall 231 of the atomization chamber comprises a step 232 and the partition 27 is supported by the step; the first outer wall 233 of the atomization chamber comprises a groove (see the joint of the upper cover 24 and lower cover 23 in FIG. 4) and the second outer wall 241 is imbedded in the groove. The second outer wall comprises a protrusion corresponding to the groove in position and shape, and the upper cover 24 is integrated with the lower cover 23 via the cooperation of the protrusion and the groove.

As shown in FIG. 5, the partition 27 comprises a main body 270 and a spiral duct 271 disposed in the central part of the main body; the spiral duct 271 comprises a first opening 273 disposed on the top surface of the main body and a second opening 272 disposed on the bottom surface of the main body. The essential oil atomized in the atomization chamber 25 enters the accommodation chamber 26 through the spiral duct 271. As shown in FIG. 5, the partition 27 comprises a first part 274 and a second part 275 overlapping with each other, and each part is provided with arc-shaped, upward or downward depressions at different positions with its center as the circle center. When the first part 274 and the second part 275 overlap with each other according to the set position or angle, the contact surface thereof and the depressions are combined to form the spiral duct 271 comprising the first opening 273 and the second opening 272. In this example, such two parts overlap with each other, thus facilitating the fabrication, and the processing cost of the spiral duct of the disclosure is much lower than that of the one obtained by one-time molding. Optionally, in other cases, for example, when one or more through holes penetrating both sides of the partition 27 are used as air ducts, it is not necessary to overlap the two parts to obtain the partition 27. In this way, it is only necessary to select a plate with appropriate thickness and process one or more through holes on the plate, which further reduces the processing cost of the air duct. The height of the step 232 is equal to that of an edge 276 of the main body 270; the partition 27 is disposed on the step 232, and the edge 276 of the main body 270 abuts against and is flush with the first inner wall 231 of the atomization chamber; the upper cover 24 is connected to the lower cover 23, and the second inner wall 241 of the accommodation chamber abuts against the edge 276 of the main body and the first inner wall 231 of the atomization chamber to fix the partition 27. In certain embodiments, for example, when using a through hole as an air duct, the height of the step 232 is equal to the thickness of the partition 27.

Based on the structure, the upper and lower covers are integrated with the partition. In this embodiment, the bottom end of the lower cover 23 is in contact with the wall around the bottom opening of the second housing 21, so that the downward force borne by the lower cover 23 can be transmitted to the second housing 21. Thus, the external force borne by the essential oil atomization module 2 can be transmitted to the second housing 21 through the lower cover 23, thus protecting the connecting structures of the upper and lower covers, so that these structures will not be subjected to direct force or scattered force. Therefore, the durability of the whole structure is improved. In addition, in addition to reducing noise, the spiral duct 271 also plays an important role in adjusting the overflow of the atomized essential oil. It is well-known when the essential oil is atomized, the higher the air pressure is, the higher the atomization degree is. However, higher air pressure makes more air pass through the air duct per unit time, that is, the atomization amount is large, and thus, the consumption of the essential oil is large. The spiral duct 271 can not only reduce the atomized particles, but also control the overflow amount, that is, save the consumption of the essential oil. This is because the speed of the atomized essential oil passing through the spiral duct 271 is much slower than that of the direct air channel (i.e. one or more through holes connecting both sides of the partition 27). In the process of passing through the spiral duct 271, a part of the atomized essential oil recondenses into large droplets, and flows back to the atomization chamber 25 along the inner surface of the spiral air duct 271, and then returns to the essential oil container 5, which can not only improve the atomization quality, but also control the use amount of the essential oil.

In this example, the water container 14 of the water atomization assembly 1 comprises a bottom wall provided with a water outlet; the water atomization assembly further comprises a water passage 15 communicating with the water outlet, a vapor passage 18, and a blower 17; the ultrasonic atomization module 16 is disposed below the water passage 15; the blower 17 is fixedly disposed on the bottom end of the first housing 11 and is configured to produce airflow to drive the vapor in the vapor passage 18 to flow out of the vapor outlet 12 and mix with the ambient air. Optionally, the perfume outlet 22 of the second housing 21 is disposed on one side and communicates with the vapor passage 18, so that the atomized essential oil and vapor are premixed in the vapor passage 18, and then overflow from the vapor outlet 12 into the ambient air, as shown in FIG. 3. A buoy valve is disposed between the water outlet and the water passage 15; the buoy valve comprises a control valve disposed at the water outlet and a telltale float disposed in the water passage and matched with the control valve. In this embodiment, the top of the water container 14 is provided with a water inlet, so that water can be added directly without taking out the water container 14, which is convenient for operation. Meanwhile, in this embodiment, transparent observation windows are disposed at different positions of the water container 14 and the water passage 15, so that the user can watch the water level at any time, so as to add water or stop the device when there is a lack of water.

In certain embodiments, the device further comprises a third housing 31 and a control unit 3 disposed in the third housing 31; the control unit is configured to control the working time and/or working state of the ultrasonic atomization module and the essential oil atomization module 2. Specifically, the control unit controls the working time and other working parameters of the vacuum pump 6, the blower 17 and ultrasonic atomization module 16. Furthermore, the control unit 3 can control the water atomization module and the essential oil atomization assembly to work independently or simultaneously. The third housing further comprises a multi-position selective switch and a timing switch for separately controlling the atomization of water and essential oil. In this example, the third housing is fixedly embedded in the lower part of the recess. In this way, even if there is less water in the water container 14, it can be easy to operate the control unit 3 without pushing the entire device. At the same time, the arrangement of the groove 4 also makes the operation more convenient to dispose the essential oil container 5 on the essential oil atomization module 2. Furthermore, the device of the disclosure also has the dry burning prevention function. Specifically, the control unit 3 has a water shortage detection circuit, which comprises a high-frequency oscillation circuit; the high-frequency oscillation circuit comprises a piezoelectric sheet and a bias circuit; one side of the piezoelectric sheet is placed in water, the other side is exposed to air. The bias circuit of the high-frequency oscillation circuit has a voltage detection circuit. The voltage detection circuit determines whether there is water in the piezoelectric sheet of the high-frequency oscillation circuit by detecting the bias voltage of the high-frequency oscillation circuit.

It will be obvious to those skilled in the art that changes and modifications may be made, and therefore, the aim in the appended claims is to cover all such changes and modifications.

What is claimed is:

1. A device, comprising:

a water atomization assembly, the water atomization assembly comprising a first housing, a water container disposed in the first housing, an ultrasonic atomization module disposed in the first housing to atomize water from the water container;

an essential oil atomization assembly, the essential oil atomization assembly comprising a second housing, an essential oil atomization module disposed in the second housing, and an essential oil container;

a vacuum pump fixedly disposed on a bottom end of the first housing; wherein:

the essential oil atomization module is connected to and disposed above the essential oil container; the essential oil container is at least partially disposed in the second housing;

the first housing comprises an outer wall comprising a recess, and the second housing is fixedly embedded in an upper part of the recess; and the vacuum pump is connected to the essential oil atomization module to provide compressed air to atomize an essential oil from the essential oil container.

2. The device of claim 1, wherein the second housing comprises an inner side wall and a mounting member protruding from the inner side wall; and the essential oil atomization module is fixed on the mounting member through a screw fastener.

3. The device of claim 2, wherein the mounting member comprises two mounting columns protruding from the second housing; and the essential oil atomization module comprises screw holes corresponding to the two mounting columns in positions and sizes.

4. The device of claim 3, wherein the essential oil atomization module comprises a nozzle, an upper cover, a partition, and a lower cover; the nozzle is disposed on a side wall of the lower cover; the partition is disposed on the lower cover; the partition and the lower cover form an atomization chamber, and the partition and the upper cover form an accommodation chamber; the partition comprises an air channel, and the atomization chamber communicates with the accommodation chamber via the air channel.

5. The device of claim 4, wherein the lower cover comprises a first through hole and a second through hole, both communicating with the atomization chamber; the first through hole is disposed on a lower part of the lower cover; the second housing further comprises a bottom opening; the essential oil container comprises a head passing through the bottom opening of the second housing to communicate with the first through hole; the second through hole is disposed on a side part of the lower cover to receive the nozzle; one end of the nozzle close to the atomization chamber is connected to an air duct, and the compressed air passes through the nozzle and the air duct and enters the atomization chamber; another end of the air duct is provided with and communicates with a straw; the straw extends through the head and into the essential oil container.

6. The device of claim 5, wherein the atomization chamber comprises a first inner wall and a first outer wall; the accommodation chamber comprises a second inner wall and a second outer wall; the first inner wall comprises a step and the partition is supported by the step; the first outer wall comprises a groove and the second outer wall is imbedded in the groove; the second outer wall comprises a protrusion corresponding to the groove in position and shape, and the upper cover is integrated with the lower cover via the cooperation of the protrusion and the groove.

7. The device of claim 6, wherein the partition comprises a main body and a spiral duct disposed in a central part of the main body; the spiral duct comprises a first opening disposed on a top surface of the main body and a second opening disposed on a bottom surface of the main body; and the essential oil atomized in the atomization chamber enters the accommodation chamber through the spiral duct.

8. The device of claim 7, wherein a height of the step is equal to that of an edge of the main body; the partition is disposed on the step, and the edge of the main body abuts against and is flush with the first inner wall of the atomization chamber; the upper cover is connected to the lower cover, and the second inner wall of the accommodation chamber abuts against the edge of the main body and the first inner wall of the atomization chamber to fix the partition.

9. The device of claim 8, wherein the water container comprises a bottom wall provided with a water outlet; the water atomization assembly further comprises a water passage communicating with the water outlet, a vapor passage, and a blower; the ultrasonic atomization module is disposed below the water passage; the blower is fixedly disposed on the bottom end of the first housing and is configured to produce airflow to drive vapor in the vapor passage to flow out.

10. The device of claim 9, wherein a buoy valve is disposed between the water outlet and the water passage; the buoy valve comprises a control valve disposed at the water outlet and a telltale float disposed in the water passage and matched with the control valve.

11. The device of claim 10, wherein the second housing comprises a perfume outlet communicating with the vapor passage, so that atomized essential oil and vapor are premixed in the vapor passage, and then overflow from the vapor outlet into ambient air.

12. The device of claim 1, further comprises a third housing and a control unit disposed in the third housing; wherein the control unit is configured to control a working time and/or working state of the ultrasonic atomization module and the essential oil atomization module; and the third housing is fixedly embedded in a lower part of the recess.

* * * * *